US00PP31347P2

(12) United States Plant Patent
Gmitter, Jr.

(10) Patent No.: US PP31,347 P2
(45) Date of Patent: Jan. 14, 2020

(54) MANDARIN TREE NAMED 'MARATHON'

(50) Latin Name: ***Citrus reticulata* hybrid**
Varietal Denomination: Marathon

(71) Applicant: Florida Foundation Seed Producers, Inc., Marianna, FL (US)

(72) Inventor: Frederick G. Gmitter, Jr., Lakeland, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 15/998,369

(22) Filed: Aug. 8, 2018

(51) Int. Cl.
*A01H 5/08* (2018.01)
*A01H 6/78* (2018.01)

(52) U.S. Cl.
USPC ..... Plt./202

(58) Field of Classification Search
USPC ..... Plt./202
See application file for complete search history.

(56) References Cited

U.S. PATENT DOCUMENTS

| | | | |
|---|---|---|---|
| PP21,356 | P3 | 10/2010 | Gmitter et al. |
| PP26,086 | P3 | 11/2015 | Grosser |
| PP27,145 | P3 | 9/2016 | Grosser |
| PP27,581 | P2 | 1/2017 | Chaparro et al. |
| PP27,829 | P3 | 4/2017 | Grosser |
| PP29,091 | P3 | 3/2018 | Grosser |

OTHER PUBLICATIONS

U.S. Appl. No. 15/998,370, filed Aug. 8, 2018, Gmitter.

Vardi, et al., "Induction of Seedlessness in Citrus: From Classical Techniques to Emerging Biotechnological Approaches," *J Amer Soc Hort Sci* 133(1):117-126, 2008.

*Primary Examiner* — Annette H Para
(74) *Attorney, Agent, or Firm* — Dentons US LLP

(57) ABSTRACT

'Marathon' is a new and distinct hybrid cultivar of mandarin tree (*Citrus reticulata*) distinguished at least by its seedless, easy-to-peel, and well-colored fruit, the early maturation of its fruit, and the above average length that its fruit can be held on the tree without deterioration.

6 Drawing Sheets

Latin name of the genus and species of the plant claimed: *Citrus reticulata* hybrid.

Variety denomination: 'Marathon'.

BACKGROUND OF THE INVENTION

The present invention relates to a new and distinct hybrid cultivar of mandarin tree (*Citrus reticulata*) designated 'Marathon'. 'Marathon' can be distinguished at least by its seedless, easy-to-peel, and well-colored fruit, the early maturation of its fruit, and the above average length that its fruit can be held on the tree without deterioration.

'Marathon' was derived from a seedling tree that was itself selected from a family of hybrids that was produced by a cross performed at Lake Alfred, Fla. in the spring of 2005. The seed parent was the mandarin variety 'Daisy' (unpatented), which was produced by crossing the mandarin varieties 'Fortune' (unpatented) and 'Fremont' (unpatented). The pollen parent was the small-fruited mandarin cultivar 'Seedless Kishu' (unpatented), which is also known as 'Mukakukishu' in Japan. The original seedling tree was planted in the field at Lake Alfred, Fla. in the spring of 2007 and was first selected during the autumn of 2013. 'Marathon' was first asexually propagated in October, 2014 at Vero Beach, Fla. by top working it onto existing red grapefruit trees growing on 'Swingle' citrumelo (unpatented) rootstock. 'Marathon' was also grafted onto sour orange seedling rootstocks that were planted in both Vero Beach, Fla. and Lake Alfred, Fla.

SUMMARY OF THE INVENTION

The following are characteristics of 'Marathon' when grown under normal horticultural practices in central Florida: 'Marathon' produces annual crops of well-colored fruit that are seedless, easy-to-peel, early maturing, and able to be held on the tree as late as January.

'Marathon' differs from its parents and all other known *Citrus* varieties. 'Marathon' trees can be readily and unambiguously distinguished from those of its parents 'Daisy' and 'Seedless Kishu' at least based upon the time of year during which their fruit matures; fruit seed content, firmness, and size; ease with which the peel can be removed from the fruit; and the rate at which the fruit deteriorates when held on the tree. The fruit of 'Marathon' is medium-sized and very firm. The fruit of 'Daisy' is medium-sized and firm. The fruit of 'Seedless Kishu' is small-sized and soft. The fruit of 'Marathon' matures in late August through early September, whereas, the fruit of 'Daisy' and 'Seedless Kishu' mature respectively in mid-November and October, with substantial variation among the fruit of 'Seedless Kishu' (even within a single tree). The fruit of 'Daisy' are seeded (1-3 seeds per segment), but the fruit of 'Marathon' and 'Seedless Kishu' are completely seedless even with cross-pollination. The fruit of 'Seedless Kishu' exhibits very poor on-tree storage ability, i.e., quickly deteriorates; the fruit of 'Daisy' can hold on the tree for several weeks before deteriorating; and the fruit of 'Marathon' can hold on the tree in good condition for several months without deteriorating. The fruit of 'Daisy' are moderately difficult to peel; the fruit 'Marathon' are easy to peel; and the fruit of 'Seedless Kishu' are very easy to peel. 'Daisy' trees are prone to an alternate fruit bearing habit; whereas, both 'Marathon' and 'Seedless Kishu' bear fruity annually.

'Marathon' trees can also be readily and unambiguously distinguished from 'Clementine' trees. The two varieties have overlapping fruit maturity windows and bear fruit annually, but the fruit of 'Clementine', which is medium to small-sized, cannot hold on the trees for months without deteriorating like the firm, medium-sized fruit of 'Marathon'. Instead, 'Clementine' fruit quickly goes from moderately firm to soft. Also, the fruit of 'Clementine' are only seedless in the absence of cross-pollination, and the peel of 'Clementine' fruit is more difficult to remove than that of 'Marathon'.

BRIEF DESCRIPTION OF THE DRAWINGS

This new hybrid mandarin tree is illustrated by the accompanying photographs captured in 2014 (FIGS. 2-5) and 2016 (FIGS. 1 and 6), which show a tree's typical form, foliage, fruit, and flower. The colors shown are as true as can be reasonably obtained by conventional photographic procedures.

DETAILED BOTANICAL DESCRIPTION

Figure 1:
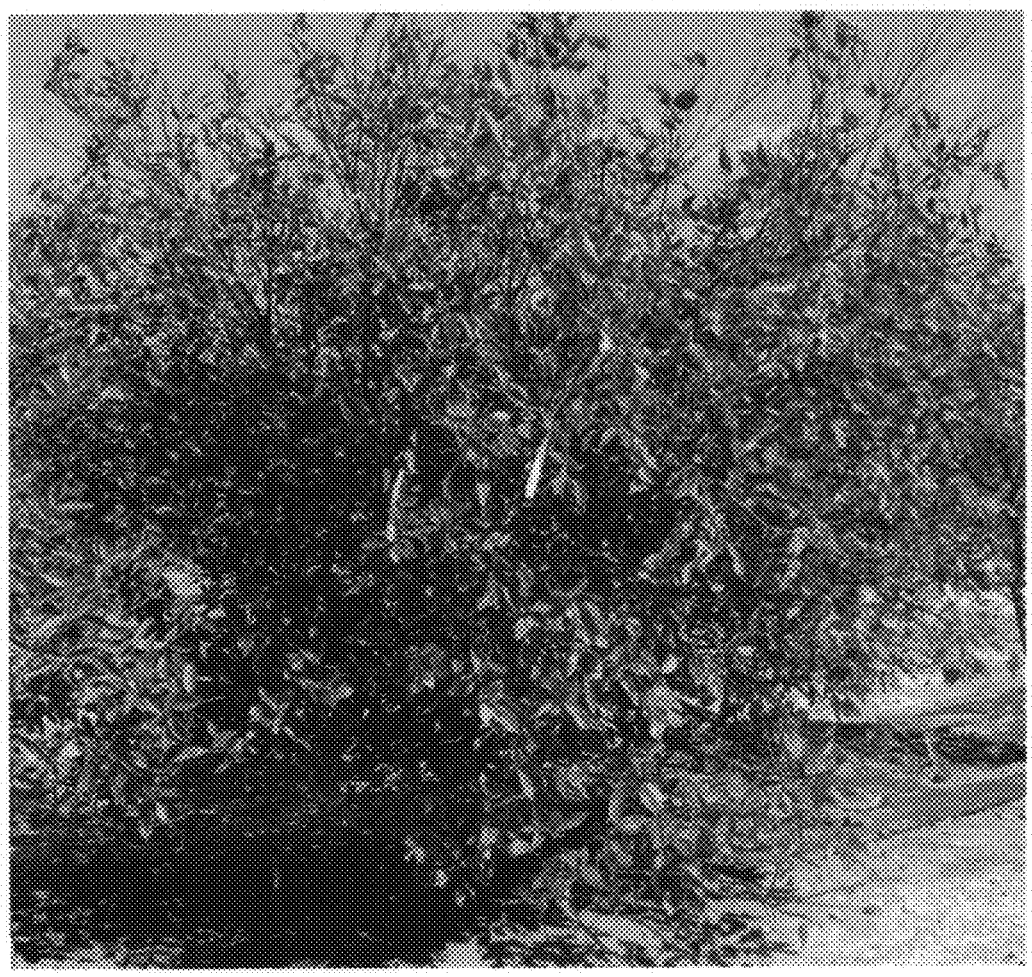
FIG. 1—Shows the overall habit of the original 'Marathon' seedling tree growing on its own roots at approximately 9-years-old in the late winter as it is beginning to decline from Huanglongbing.
Figure 2:
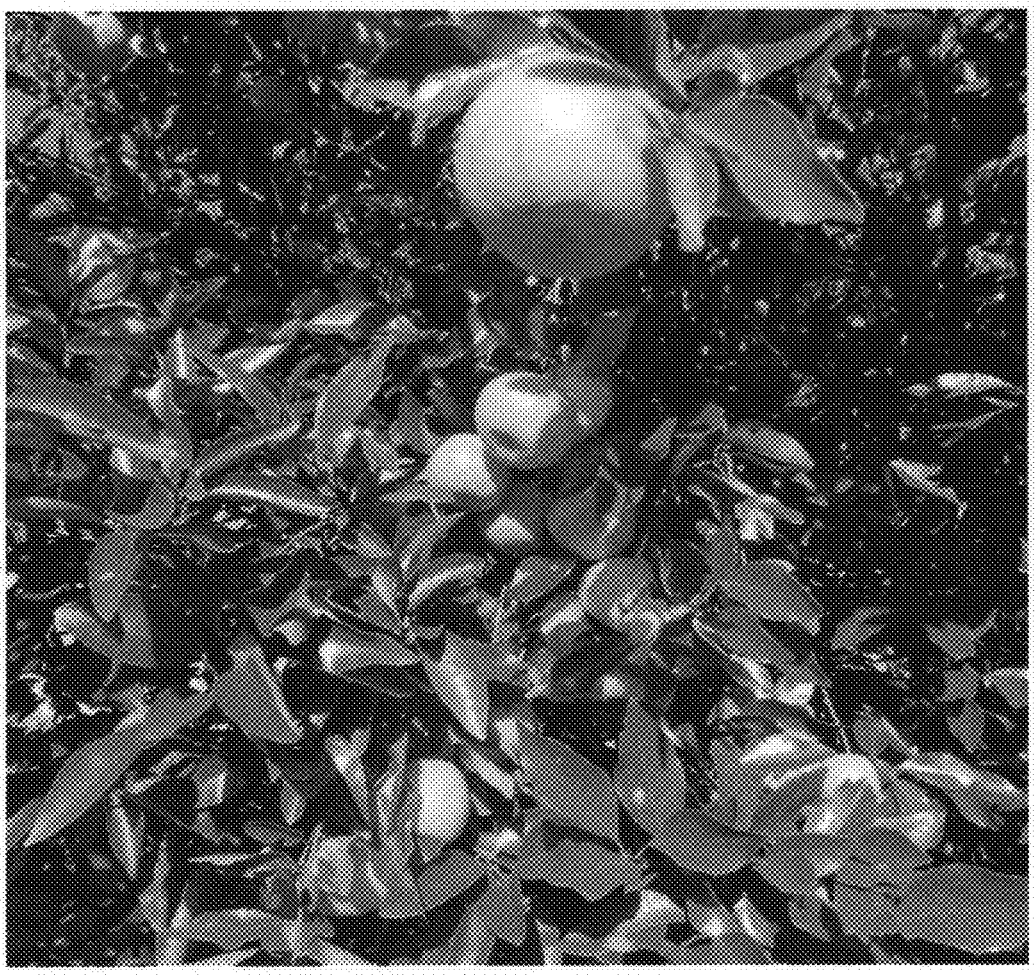
FIG. 2—Shows a close-up of the mature fruit-bearing habit within the canopy of the original 'Marathon' seedling tree during autumn.
Figure 3:
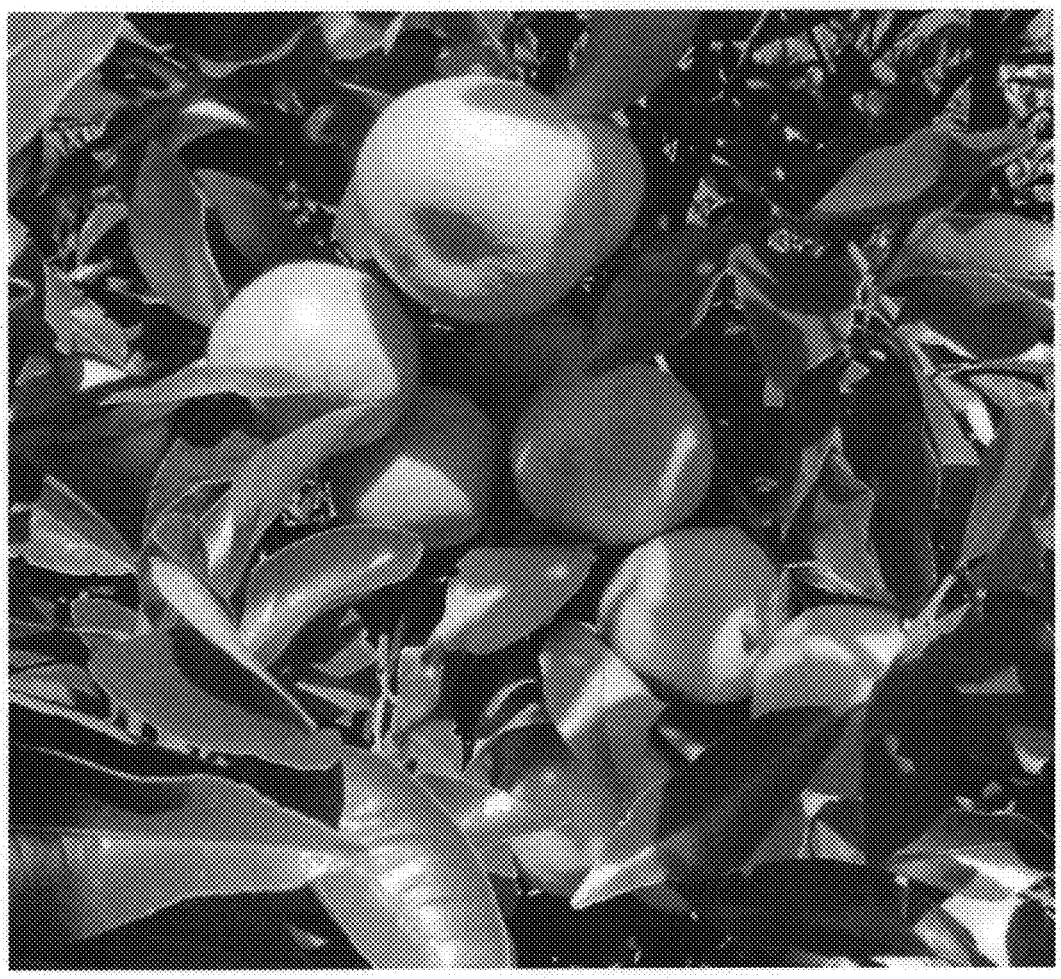
FIG. 3—Shows a close-up of the leaves and mature fruit of the original 'Marathon' seedling tree during autumn.
Figure 4:
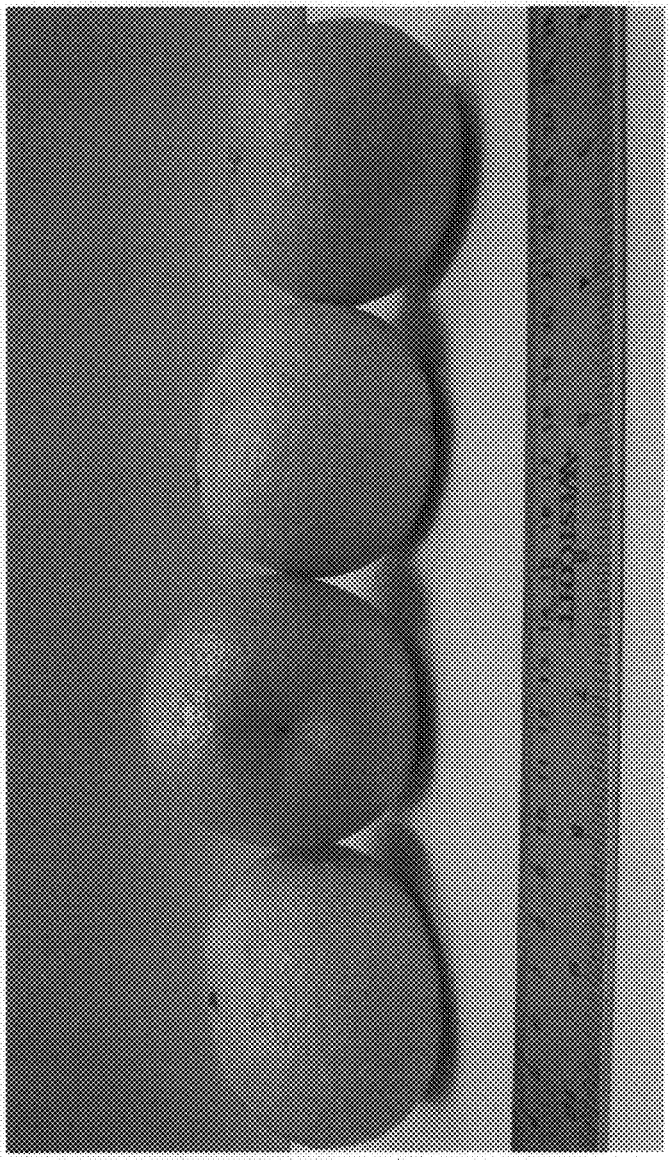
FIG. 4—Shows a close-up of fruit, with the rind present, that were obtained during autumn from the original 'Marathon' seedling tree.
Figure 5:
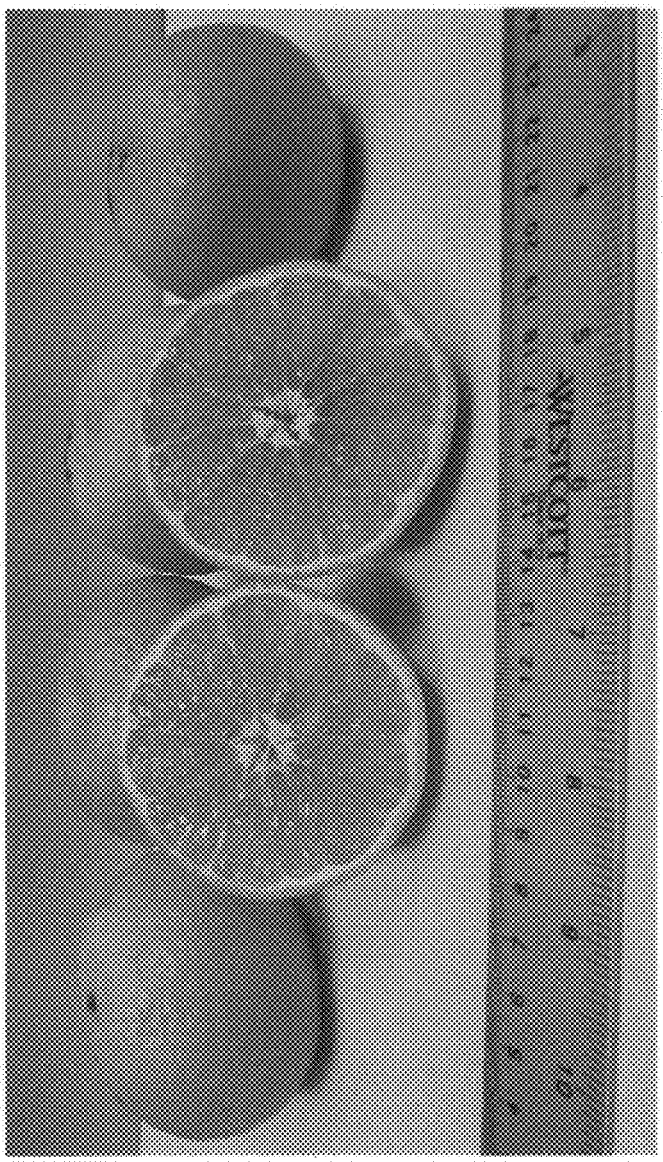
FIG. 5—Shows a close-up of a fruit cut cross-sectionally that was obtained during autumn from the original 'Marathon' seedling tree.
Figure 6:
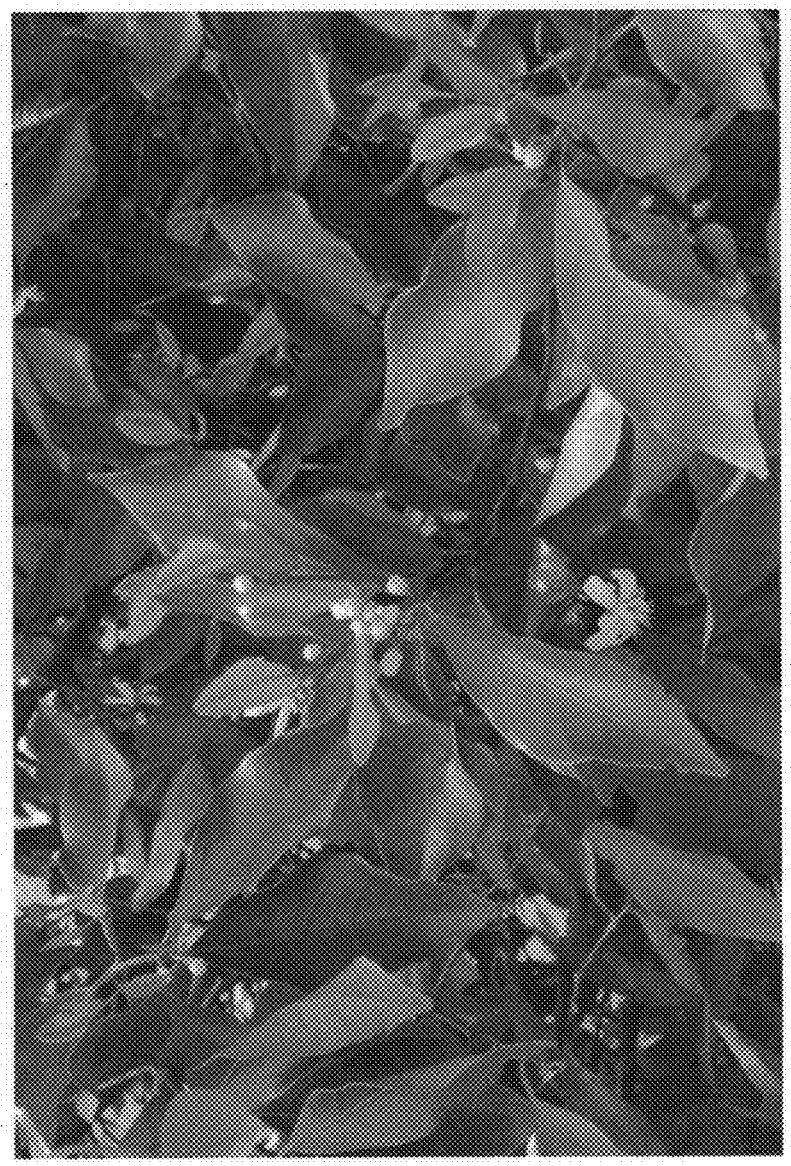
FIG. 6—Shows a close-up of the original 'Marathon' seedling tree during April with old foliage, spring flush, and flowers.

The following detailed description sets forth distinctive characteristics of 'Marathon'. The data that define these characteristics were collected from a 9-year-old tree growing on its own roots at Lake Alfred, Fla. 'Marathon' has not been observed under all possible environmental conditions, and the measurements given may vary when grown in different environments. Further, certain characteristics may vary with plant age. Color descriptions, except those recited in common terms, are based on The Royal Horticultural Society (R.H.S.) Colour Chart, 2nd Edition, which was published in London by the R.H.S. in association with Flower Council of Holland. If any R.H.S. color designations below differ from the accompanying photographs, the R.H.S. color designations are accurate.

Classification:

*Botanical.*—*Citrus reticulata* hybrid.

*Common name.*—Mandarin hybrid or Tangerine.

Parentage:

*Female parent.*—'Daisy' mandarin.

*Male parent.*—'Seedless Kishu' small-fruited mandarin.

Tree:

*Ploidy.*—Diploid.

*Size.*—Medium.

*Height.*—2.1 m.

*Tree spread.*—2.1-2.5 m.

*Vigor.*—Vigorous.

*Density.*—Canopies are quite dense.

*Form.*—The tree is round shaped with lateral and upright branches growing toward low to medium angles. Branches with fruit exhibited drooping.

*Growth habit.*—Both upright and lateral growth with low medium angle.

Trunk and branches:

*Trunk diameter.*—10.8 cm in diameter at 30 cm above from ground.

*Trunk texture.*—Smooth.

*Trunk bark color.*—RHS 199A (grey-brown) and irregularly striated with RHS N189A (greyed-green).

*Crotch angle.*—First crotch from 45-50 degree angle, middle crotch formed 30 degree angle.

*Branch length.*—Branch reaches 2.5 meters from the first crotch to the tip of the branch.

*Branch texture.*—Relatively smooth occasionally with small thorns or spines.

*Branch color* (*shoots from previous flush, hardened and* 4-5 *mm in diameter*).—RHS 137A (green).

Leaves:

*Size* (*lamina average*).—Length: 98.5 mm. Width: 50 mm. L/W ratio: 1.97.

*Thickness.*—Regular and average compared to other commercial mandarin hybrids.

*Type.*—Simple.

*Shape.*—Elliptical.

*Apex.*—Retuse.

*Base.*—Acute to sub-obtuse.

*Margin.*—Entire and slightly undulate.

*Surface.*—Upper surface: Glabrous. Lower surface: Medium veins that are pinnately netted.

*Color.*—Upper surface (adaxial): RHS 137A (green). Lower surface (abaxial): RHS 146B (yellow-green).

*Petiole.*—Shape: Brevipetiolate (shorter than leaf lamina) and the junction between petiole and lamina is articulate. Width (petiole wing): Very narrow. Shape (petiole wing): Obovate. Length: 9.5-15.0 mm. Width: 2.5-2.8 mm. Color: RHS 137A (green).

Flowers:

*Type.*—Hermaphrodite.

*Bearing.*—Flower grown from leaf axillaries and leaf terminals in single and in small clusters, most single flowers grown from leaf axillaries, each flower branch consists of 8-12 flowers.

*Flower diameter.*—Fully open flower with average diameter of 28.1-28.5 mm.

*Flower depth.*—Typical flower with average depth of 14 mm.

*Flower blooming period.*—First bloom observed Apr. 2, 2016. Full bloom observed Apr. 7, 2016. Earlier flowering is more common in other seasons.

*Flower bud size.*—Length: Initial visible flower bud with 1.5 mm in length; mature flower bud with 16 mm in length. Diameter: Initial visible flower bud with 2.0 mm in diameter; mature flower bud with 8.1 mm in diameter.

*Shape.*—Initial visible flower bud with round ball shape; mature flower bud with elongated olive shape.

*Color.*—RHS 145B (yellow-green) for initial visible flower bud; RHS NN155C (white) for mature flower bud with RHS 150C (yellow-green) spots distributed at tip of the flower bud.

*Flower petals*.—Size: Length: 13.7 mm. Width: 8.0 mm. Shape: Flat spatula shaped. Apex shape: Smooth acute shaped. Base shape: Even obtuse. Color: Up surface with RHS NN155A (white); lower surface with RHS NN155B (white) with RHS 150C (yellow-green) spots distributed toward to the petal apex. Margin: Smooth.

*Flower sepal*.—Number: 5 per flower. Shape: Delta shaped with acute angle at apex. Length: 1.2 mm. Width: 1.8 mm. Apex shape: Triangle shaped. Margin: Smooth. Color: Upper surface with RHS 145C (yellow-green); lower surface with RHS N144C (yellow-green).

*Fragrance*.—Moderately fragrant.

*Flower pedicel*.—Length: 4.9-5.0 mm. Diameter: 1.0-1.1 mm. Color: RHS 145A (yellow-green).

Reproductive organs:

*Fertility*.—Appears self-fertile.

*Stamen length*.—9.2-9.4 mm.

*Anther length*.—2.0 mm.

*Anther width*.—0.8-1.0 mm.

*Anther color*.—RHS 10A (yellow).

*Anther filament length*.—7.5-7.8 mm.

*Pollen amount*.—Abundant.

*Pollen color* (*general*).—RHS 9A (yellow).

*Pistil number*.—1.

*Pistil length*.—6.0-6.5 mm.

*Pistil color*.—RHS 145B (yellow-green).

*Style length*.—5.5 mm.

*Style diameter*.—1.2-1.3 mm.

*Style color*.—RHS 145B (yellow-green).

*Ovary shape*.—Oval shaped.

*Ovary*.—diameter: 2.7 mm.

*Ovary color*.—RHS 143C (green).

Fruit:

*Size*.—Uniform. Tall: 49.2-51.0 mm in average. Width: 59.3-60.0 mm in average.

*Average weight* (*per individual fruit*).—94.5 grams.

*Shape*.—Round.

*Shape* (*cross-section*).—Round.

*Apex*.—Truncated with shallow dent.

*Apex cavity diameter*.—No cavity.

*Base cavity diameter*.—2.4-2.6 mm.

*Base*.—Very short necked and wrinkled.

*Maturity*.—First pick around Aug. 20, 2015 (based on season and rootstock); last pick around Jan. 14, 2016 though fruit continue to hold on the tree for a longer time (based on season and rootstock).

*Fruit stem* (*short stem connecting the fruit*).—Length: 4.0 mm. Diameter: 2.5 mm. Color: RHS 137B (green) with RHS 199B (grey-brown) strip.

Rind:

*Adherence*.—Adherence between albedo (mesocarp) and flesh (endocarp) is medium. The adherence is evenly distributed from based to apex.

*Thickness*.—2.2-2.3 mm in average.

*Texture*.—Smooth.

*Color*.—Flavedo (epicarp): Ranges between RHS 25A (orange) to RHS 24A (orange). Albedo (mesocarp): RHS 11B (yellow).

*Stylar end*.—Closed.

*Rind oil cell density*.—98-100 oil cells/square cm.

Flesh:

*Number of segments*.—Average between 10-12 segments per fruit.

*Segment walls*.—Medium soft with sufficient strength to maintain integrity as separated.

*Juice*.—Abundant.

*Color*.—Uniformly RHS 24B (orange).

*Texture*.—Medium soft.

*Vesicles*.—Length: arranged from 10-11 mm in average. Diameter (thickness): 2.9-3.0 mm in average.

*Eating quality* (*varies from season to season*).—Soluble solids (average): 12.5-17.4 Brix (tested from mid-August through late December). Acidity (average): 0.9-0.6% (decreasing, tested from mid-August through late December). Ratio: 14-28, increasing through the season.

Seeds: Seedless.

What is claimed is:

1. A new and distinct hybrid cultivar of mandarin tree (*Citrus reticulata*) named 'Marathon', as illustrated and described herein.

* * * * *